(12) United States Patent
Kolhe et al.

(10) Patent No.: US 11,896,594 B2
(45) Date of Patent: Feb. 13, 2024

(54) PALATABLE ANTIPARASITIC FORMULATIONS

(71) Applicant: Zoetis Services LLC, Parsippany, NJ (US)

(72) Inventors: Sachin Pundlik Kolhe, Navi Mumbai (IN); Supriya Gautam Thakur, Mumbai (IN)

(73) Assignee: Zoetis Services LLC, Parsippany, NJ (US)

( * ) Notice: Subject to any disclaimer, the term of this patent is extended or adjusted under 35 U.S.C. 154(b) by 538 days.

(21) Appl. No.: 17/273,111

(22) PCT Filed: Sep. 3, 2019

(86) PCT No.: PCT/US2019/049279
§ 371 (c)(1),
(2) Date: Mar. 3, 2021

(87) PCT Pub. No.: WO2020/051106
PCT Pub. Date: Mar. 12, 2020

(65) Prior Publication Data
US 2021/0220360 A1    Jul. 22, 2021

Related U.S. Application Data

(60) Provisional application No. 62/727,018, filed on Sep. 5, 2018.

(51) Int. Cl.
| | |
|---|---|
| *A61K 31/506* | (2006.01) |
| *A61P 33/00* | (2006.01) |
| *A61K 9/00* | (2006.01) |
| *A61K 9/20* | (2006.01) |
| *A61K 31/365* | (2006.01) |
| *A61K 31/422* | (2006.01) |
| *A61K 31/7048* | (2006.01) |

(52) U.S. Cl.
CPC .......... *A61K 31/506* (2013.01); *A61K 9/0056* (2013.01); *A61K 9/2018* (2013.01); *A61K 9/2054* (2013.01); *A61K 9/2068* (2013.01); *A61K 31/365* (2013.01); *A61K 31/422* (2013.01); *A61K 31/7048* (2013.01); *A61P 33/00* (2018.01)

(58) Field of Classification Search
None
See application file for complete search history.

(56) References Cited

U.S. PATENT DOCUMENTS

| | | |
|---|---|---|
| 2002/0081292 A1 | 6/2002 | Jancys |
| 2015/0209355 A1 | 7/2015 | Chubb et al. |
| 2016/0051524 A1 | 2/2016 | de Rose et al. |
| 2017/0354593 A1 | 12/2017 | Majumdar et al. |

FOREIGN PATENT DOCUMENTS

| | | | |
|---|---|---|---|
| AU | 2006100657 A4 | * | 9/2006 |
| RU | 2 657 508 C1 | | 6/2018 |

OTHER PUBLICATIONS

Aleo M, Ross S, Becskei C, Coscarelli E, King V, Darling M, Lorenz J. Palatability testing of oral chewables in veterinary medicine for dogs. Open Journal of Veterinary Medicine. Aug. 27, 2018;8(8):107-18.*

* cited by examiner

*Primary Examiner* — Patrick T Lewis
(74) *Attorney, Agent, or Firm* — Paul M. Misiak

(57) ABSTRACT

The present invention is directed to a palatable, hard chewable composition comprising a therapeutically effective amount of a veterinary acceptable isoxazoline, a stabilized macrocyclic lactone, an acceptable salt form of pyrantel, at least one natural animal based palatant, and at least one veterinary acceptable excipient; and methods for treating or preventing a parasitic infection or infestation in an animal in need thereof with said composition.

12 Claims, No Drawings

PALATABLE ANTIPARASITIC FORMULATIONS

CROSS-REFERENCE TO RELATED APPLICATIONS

This application is a US National Stage entry of International Application No. PCT/US2019/049279, filed Sep. 3, 2019, which claims the benefit of U.S. Provisional Application No. 62/727,018, filed Sep. 5, 2018.

FIELD OF INVENTION

The invention describes a palatable, hard chewable composition that comprises at least one veterinary acceptable isoxazoline, a stabilized macrocyclic lactone, an acceptable salt form of pyrantel, at least one natural animal based palatant, and at least one veterinary acceptable excipient. The palatable composition is compressed into a hard tablet. The invention also contemplates a method of use for treating and/or preventing a parasitic infection or infestation in an animal in need thereof by administering said composition to the animal.

BACKGROUND OF INVENTION

Formulation of a drug (i.e., active agent) into an edible medication, such as a palatable, chewable dosage form, can increase subject acceptance of the medication, especially animals that tend to resist swallowing hard tablets or capsules and chewing bitter and/or granular dosage forms. Flavorings (palatants) and polymeric coatings have commonly been used to provide some degree of palatability to the dosage form. Besides palatability, compositions comprising more than one veterinary agent, i.e., antiparasitic agent, tend to have issues with stability because some agents are acid labile while others are base labile. A veterinary antiparasitic composition comprising at least two antiparasitic agents that is dosed monthly to animals needs to be stable and palatable to ensure product safety, efficacy, and compliance. In some instances, palatable compositions have been prepared for canine oral consumption based on compositions that are soft or gummy which are prepared by using glycerin, fats, and oils. The present invention achieves a palatable, hard chewable composition that is stable, safe and efficacious against ectoparasites and endoparasites and can be prepared by typical rotary compression, rather than formed by extrusion or punch cutting.

SUMMARY OF THE INVENTION

In accordance with this invention, it has been discovered that the oral hard chewable composition of the invention is stable, palatable, safe, and efficacious against ectoparasites and endoparasites when administered monthly. Increased stability correlates with increased shelf-life, and optimally, efficacy, while palatability increases patient compliance.

In one aspect of the invention is a palatable, hard chewable tablet veterinary composition comprising a) a therapeutically effective amount of a veterinary acceptable isoxazoline; b) a stabilized macrocyclic lactone; c) an acceptable salt form of pyrantel, d) at least one natural based palatant; e) at least one veterinary acceptable excipient; and optionally, f) at least one additional antiparasitic agent. In another aspect, is a palatable, hard chewable tablet veterinary composition comprising a) a therapeutically effective amount of a veterinary acceptable isoxazoline; b) a stabilized macrocyclic lactone; c) an acceptable salt form of pyrantel, d) at least one natural animal based palatant; e) at least one veterinary acceptable excipient; and f) at least one additional antiparasitic agent. In another aspect, is a palatable, hard chewable tablet veterinary composition comprising a) a therapeutically effective amount of sarolaner; b) stabilized moxidectin; c) pyrantel pamoate, d) at least one natural animal based palatant; and e) at least one veterinary acceptable excipient. In another aspect, is a palatable, hard chewable tablet veterinary composition comprising a) a therapeutically effective amount of sarolaner; b) stabilized moxidectin; c) pyrantel pamoate, d) at least one natural animal meat based palatant; and e) at least one veterinary acceptable excipient.

In one aspect of the invention, the isoxazoline is selected from the group consisting of sarolaner, afoxolaner, fluralaner, and lotilaner. In one aspect of the invention, the isoxazoline is sarolaner (Simparica®), (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethan-1-one, the compound of Formula (A1).

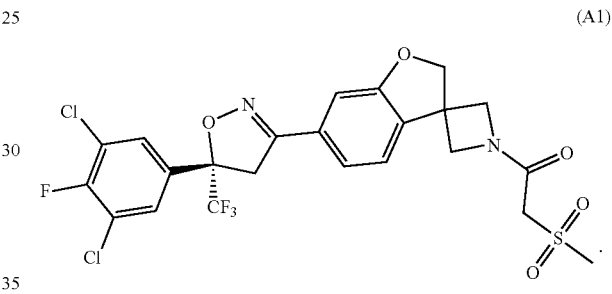

(A1)

In another aspect, the stabilized macrocyclic lactone is selected from the group consisting of moxidectin, selamectin, ivermectin, abamectin, or milbemycin oxime. In yet another aspect, the stabilized macrocyclic lactone is selected from the group consisting of moxidectin, ivermectin, or milbemycin oxime. In yet another aspect, the stabilized macrocyclic lactone is moxidectin or milbemycin oxime. In yet another aspect, the stabilized macrocyclic lactone is moxidectin. In yet another aspect, the stabilized macrocyclic lactone is milbemycin oxime. In another aspect, the veterinary acceptable isoxazoline is sarolaner and the stabilized macrocyclic lactone is moxidectin. In yet another aspect, the composition further comprises an acceptable salt form of pyrantel. In one aspect, the acceptable salt form of pyrantel is citrate, pamoate (embonate), and tartrate. In another aspect, the acceptable salt form of pyrantel is pyrantel pamoate.

In yet another aspect, the composition comprises sarolaner, stabilized moxidectin, and pyrantel pamoate. In yet another aspect, the composition comprises sarolaner, stabilized moxidectin, pyrantel pamoate, at least one natural animal based palatant, and at least one veterinary acceptable excipient. In yet another aspect, the composition comprises sarolaner, stabilized moxidectin, pyrantel pamoate, and at least one natural animal meat based palatant, and at least one veterinary acceptable excipient.

In yet another aspect, the stabilizing agent for the macrocyclic lactone is hydroxypropylmethyl cellulose. In yet another aspect, the stabilizing agent for the macrocyclic lactone is meglumine. In yet another aspect, the stabilizing agent for the macrocyclic lactone is hydroxypropylmethyl cellulose and meglumine. In yet another aspect, the stabilizing agent for the macrocyclic lactone is an antioxidant. In yet another aspect, the antioxidant is BHT. In yet another aspect, the stabilizing agents for the macrocyclic lactone, moxidectin, is hydroxypropylmethyl cellulose, meglumine, and BHT.

In yet another aspect, the amount of hydroxypropylmethyl cellulose and meglumine account for about 2 w/w % to about 4 w/w % of the total weight of the tablet. In yet another aspect, the amount of hydroxypropylmethyl cellulose and meglumine account for about 2 w/w % to about 3 w/w % of the total weight of the tablet. In yet another aspect, the amount of hydroxypropylmethyl cellulose and meglumine account for about 2.4 w/w % of the total weight of the tablet. In yet another aspect, the amount of BHT is about 0.02 w/w % of the total weight of the tablet. In yet another aspect, the composition comprises sarolaner, stabilized moxidectin, pyrantel pamoate, the stabilizing agents hydroxypropylmethyl cellulose and meglumine, and the antioxidant, BHT; wherein the stabilizing agents account for about 2 to 3 w/w % of the weight of the tablet, at least one natural animal based palatant, and at least one veterinary acceptable excipient. In yet another aspect, the composition comprises sarolaner, stabilized moxidectin, pyrantel pamoate, the stabilizing agents hydroxypropylmethyl cellulose and meglumine, and the antioxidant, BHT; wherein the stabilizing agents account for about 2-3 w/w % of the weight of the tablet, at least one natural animal based palatant, at least one veterinary acceptable excipient; and optionally at least one additional antiparasitic agent. In yet another aspect, the composition comprises sarolaner, stabilized moxidectin, pyrantel pamoate, the stabilizing agents hydroxypropylmethyl cellulose and meglumine, and the antioxidant, BHT, in the amount of about 2-3 w/w % of the total weight of the tablet, and at least one natural animal based palatant, and at least one veterinary acceptable excipient.

In yet another aspect of the invention, is a composition comprising sarolaner, stabilized moxidectin, pyrantel pamoate, at least one natural animal meat based palatant, and at least one veterinary acceptable excipient; wherein the moxidectin is stabilized with hydroxypropylmethyl cellulose, meglumine, and the antioxidant, BHT. In another aspect, the composition comprises about 1.33 w/w % sarolaner, about 0.03 w/w % stabilized moxidectin, about 16 w/w % pyrantel pamoate, about 8 to 12 w/w % of at least one natural animal meat based palatant, and about 15 w/w % of a disintegrant; and wherein the moxidectin is stabilized with hydroxypropylmethyl cellulose and meglumine, and the antioxidant, BHT; and wherein the w/w % are based on the amounts of the total weight of the tablet. In yet another aspect of the invention, is a composition comprising about 1.33 w/w % sarolaner; about 0.03 w/w % stabilized moxidectin; about 16 w/w % pyrantel pamoate; about 2.42 w/w % of a mixture of HPMC, meglumine, and BHT; about 15.2 w/w % of a disintegrant, about 19.7 w/w % of a filler, about 42 w/w % of a palatant admixture; and further comprising at least one veterinary acceptable excipient; and wherein the w/w % are based on the amounts of the total weight of the tablet. In yet another aspect of the invention, is a composition comprising about 1.33 w/w % sarolaner; about 0.03 w/w % stabilized moxidectin; about 16 w/w % pyrantel pamoate; about 2.42 w/w % of a mixture of HPMC, meglumine, and BHT; about 15.2 w/w % of a disintegrant, about 19.7 w/w % of a filler, about 42 w/w % of a palatant admixture, wherein said palatant admixture comprises about 20-25 w/w % of a natural animal meat based palatant; and further comprising at least one veterinary acceptable excipient; and wherein the w/w % are based on the amounts of the total weight of the tablet.

In yet another aspect of the invention, is a method of treating and/or preventing a parasitic infection or infestation in an animal by administering the composition comprising sarolaner, stabilized moxidectin, pyrantel pamoate, at least one natural animal based palatant, at least one stabilizing agent, and at least one veterinary acceptable excipient to the animal in need thereof. In yet another aspect, the stabilizing agent is a mixture of hydroxypropylmethyl cellulose, meglumine, and the antioxidant, BHT. In yet another aspect, is a method of treating and/or preventing a parasitic infection or infestation in an animal by administering the composition comprising about 1.33 w/w % sarolaner, about 0.03 w/w % stabilized moxidectin, about 16 w/w % pyrantel pamoate, about 42 w/w % of a palatant admixture containing at least one natural animal based palatant, and at least one veterinary acceptable excipient to the animal in need thereof; and wherein the moxidectin is stabilized with a mixture of hydroxypropylmethyl cellulose, meglumine, and the antioxidant, BHT; and wherein the w/w % are based on the amounts of the total weight of the tablet.

In yet another aspect of the invention, is a composition comprising sarolaner, stabilized moxidectin, pyrantel pamoate, at least one natural animal based palatant, at least one stabilizing agent, and at least one veterinary acceptable excipient to prepare a medicament for the use to treat and/or prevent a parasitic infection or infestation in an animal in need thereof. In yet another aspect, is a composition comprising about 1.33 w/w % sarolaner, about 0.03 w/w % stabilized moxidectin, about 16 w/w % pyrantel pamoate, about 42 w/w % of a palatant admixture containing at least one natural animal based palatant, and at least one veterinary acceptable excipient, and wherein the moxidectin is stabilized with a mixture of hydroxypropylmethyl cellulose, meglumine, and the antioxidant, BHT, to prepare a medicament for the use to treat and/or prevent a parasitic infection or infestation in an animal in need thereof; and wherein the w/w % are based on the amounts of the total weight of the tablet.

In yet another aspect of the invention, the composition of the invention is administered orally to an animal. In another aspect, the composition is a palatable, hard chewable tablet that is orally administered to an animal. In yet another aspect of the invention, the composition and subsequent compressed tablets are stable. In another aspect, the animal is a companion animal. In yet another aspect, the companion animal is canine.

Definitions

For purposes of the present invention, as described and claimed herein, the following terms and phrases are defined as follows:

"About", as used herein, refers to the indicated value of the variable and to all values of the variable that are within the experimental error of the indicated value (e.g., within the 95% confidence interval for the mean) or within 10 percent of the indicated value, whichever is greater.

"Additional antiparasitic agent(s)" as used herein, unless otherwise indicated, refers to at least one additional veterinary compound or product that provides a therapeutically effective amount of the compound or product that is useful for the treatment of a parasitic infection or infestation in an animal.

"Animal", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog (canine), cat (feline), and horse (equine). Preferred companion animals are dog and cat. More preferred is dog. Non-exclusive examples of livestock include: pig, llama, rabbits, goat, sheep, deer, elk, and cattle. More preferred livestock are pig (swine) and cattle (bovine).

"At least one", as used herein, unless otherwise indicated, refers to one or more, e.g., at least one veterinary acceptable excipient means one or more excipients, e.g., (one filler; one filler and one disintegrant; two fillers and one colorant).

"Composition of the invention", or "composition" as used herein, unless otherwise indicated, refers to a palatable, hard chewable veterinary composition intended for oral administration to an animal, preferably a canine animal. The composition is also a stable composition. The composition, methods of use thereof, and uses thereof can include the use of the transitional terms comprises, comprising, consisting of, and consisting essentially of. For example, the composition comprises an isoxazoline, a stabilized macrocyclic lactone, an acceptable salt form of pyrantel, at least one natural animal based palatant, and at least one veterinary acceptable excipient; or the composition consists of (or consists essentially of) an isoxazoline, a stabilized macrocyclic lactone, an acceptable salt form of pyrantel, at least one natural animal based palatant, and at least one veterinary acceptable excipient.

"Hard", as used herein, unless otherwise indicated, describes a tablet that can be measured by practical laboratory or manufacturing tablet hardness tester instruments to determine the breaking point and structural integrity of a tablet. The hardness values of the tablets range from about 20N to about 500N. The tablet hardness values range upward with increasing tablet size. For example, tablet hardness for the 3 mg, 6 mg, 12 mg, 24 mg, 48 mg, and 72 mg sarolaner tablets ranges from about 30-70N, 40-120N, 60-150N, 100-250N, 140-300N, and 200-400N, respectively. The respective tablet weights are about 225 mg, 450 mg, 900 mg, 1800 mg, 3600 mg, and 5400 mg. The unit of hardness measure, N, is Newtons, the measure of force needed to break the tablet. 1N is equivalent to 1 kg-m/s$^2$. Hardness is based on a combination of factors, for example, but not limited to tablet shape, surface area, thickness, active agent, excipient(s), and compression forces. Depending on tablet size, the sarolaner tablet hardness ranges from about 20N to 500N. The unit of force can also be defined in kiloponds (kp) wherein 1 kp=9.80665N.

"Infection" or Infestation", as used herein, unless otherwise indicated, refers to the state or condition of having parasites on (ectoparasites) or in the body (endoparasites).

"Macrocyclic lactone" as used herein, designates a veterinary compound in the avermectin family of compounds including, for example, ivermectin, abamectin doramectin, eprinomectin, selamectin, and the like; and also includes the milbemycin family of compounds including, for example, moxidectin, milbemycin, milbemycin oxime, and the like. A preferred macrocyclic lactone of the composition of the invention is moxidectin. The preferred macrocyclic lactone is a stabilized macrocyclic lactone. The preferred stabilized macrocyclic lactone is moxidectin.

"Palatable", as used herein, unless otherwise indicated, refers to a pleasant, acceptable, or agreeable taste.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa; but more particularly nematodes including gastro-intestinal nematodes, lungworms, and heartworms. Ectoparasites are organisms of the Arthropoda phylum (e.g., arachnids and insects) which feed through or upon the skin of its host. Preferred arachnids are of the order Acarina, e.g., ticks and mites. Preferred insects are midges, lice (sucking and chewing), fleas, mosquitos, and biting flies (stable fly, horn fly, sand fly, blow fly, horse fly, and the like). Preferred compositions of the present invention can be used for the treatment of ectoparasites and endoparasites, i.e., treatment of a parasitic infection or infestation; including fleas, ticks, mites, lice, GI nematodes, and heartworm. Parasite(s) also encompasses the different life stages of the ectoparasite and endoparasite, including eggs, pupae, and larvae which feed on or in the body.

"Therapeutically effective amount", as used herein, unless otherwise indicated, refers to an amount of one active agent or combination of active agents that treats, prevents, attenuates, ameliorates, delays, or eliminates one or more symptoms, for example, the particular parasitic infection or infestation for an antiparasitic agent.

"Stabilizing agent" and "stabilizer", as used herein, unless otherwise indicated, refers to a compound known to provide chemical and/or physical stability to one or more of the active agents and/or excipients, i.e., the macrocyclic lactones, veterinary acceptable isoxazolines, and other antiparasitic agents, and/or veterinary acceptable excipients that when combined together is more stable with the stabilizer(s) than without. For example, the stabilizing agent(s) stabilize the macrocyclic lactone, particularly, moxidectin; i.e., stabilized moxidectin.

"Stable", as used herein, unless otherwise indicated, refers to overall appearance, water content, assay, antioxidant (BHT) content, degradation products, dissolution, hardness, friability, photostability, and microbiological quality of the tableted composition in accordance with VICH GL4 and GL5 guidelines under long-term and accelerated stability temperature and humidity conditions.

"Treatment", "treating", and the like, as used herein, unless otherwise indicated, refers to reversing, alleviating, or inhibiting the parasitic infection or infestation. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection, infestation, or condition. Thus, treatment can refer to administration of the composition to the animal that is not at the time of administration afflicted with said condition. Treating also encompasses preventing the recurrence of an infection or infestation or of symptoms associated therewith as well as references to "control" (e.g., kill, repel, expel, incapacitate, deter, eliminate, alleviate, minimize, and eradicate). The phrase treating (treatment) or preventing (prevention) a parasitic infection or infestation in an animal is construed as treating/preventing both endoparasites (within the body) and ectoparasites (on the body). Treating or preventing does not necessarily infer that the animal is forever free of parasites.

"Veterinary acceptable" as used herein, unless otherwise indicated, indicates that the active agent or composition must be compatible chemically and/or toxicologically, with the other ingredients comprising a formulation, composition, and/or the animal being treated therewith. The term "pharmaceutically" acceptable has the same meaning as that recited for "veterinary" acceptable.

As used herein, percent of components of the composition refers to percentages of the total weight of the palatable, hard chewable tablet and is referred to as "% w/w" or "w/w %" which defines the mass fraction of the compositional component expressed as a percentage, determined according to the formula $m_i/m_{tot} \times 100$, wherein $m_i$ is the mass of the substance of interest present in the composition, and $m_{tot}$ is the total mass of the composition. The w/w % also defines the amount of an active ingredient(s) or other compositional component(s) (e.g., a veterinary acceptable excipient) in a granulation mixture and palatant admixture, e.g., amount of HPMC in the moxidectin granulation.

The terms "comprises", "comprising", "containing", and the like, as used herein, can have the meaning ascribed to them in U.S. patent law and are open ended (inclusive) transitional terms allowing for the presence of more than that which is recited so long as basic or novel characteristics of that which is recited is not changed by the presence of more than that which is recited, but excludes prior art embodiments. The terms are synonymous with "including", "containing", or "characterized by". The terms are broader than but still include the terms consisting (consists) of and consisting (consists) essentially of.

The terms "consisting (or consists) of" and "consisting (or consists) essentially of" likewise can have the meaning ascribed to them in U.S. patent law; and are respectively closed or partially closed transitional terms that may not allow for the presence of more than that which is recited.

DETAILED DESCRIPTION

The present invention provides a palatable, hard chewable tablet composition for oral administration of a therapeutically effective amount of a veterinary acceptable isoxazoline, stabilized macrocyclic lactone, an acceptable salt form of pyrantel, at least one natural animal based palatant, and at least one veterinary acceptable excipient. The composition optionally comprises at least one additional veterinary antiparasitic agent.

Veterinary acceptable isoxazolines with insecticidal and acaricidal efficacy are non-competitive GABA (gamma-aminobutyric acid) receptor antagonists that are much more selective for GABA receptors in insects or acarids, than for those in animals, including humans. The isoxazoline binds to chloride channels in nerve and muscle cells, which blocks the transmission of neuronal signals. Affected parasites are paralyzed and die. A preferred veterinary acceptable isoxazoline is sarolaner (Simparica®), (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethan-1-one, i.e., the compound of Formula (A1), (A1)

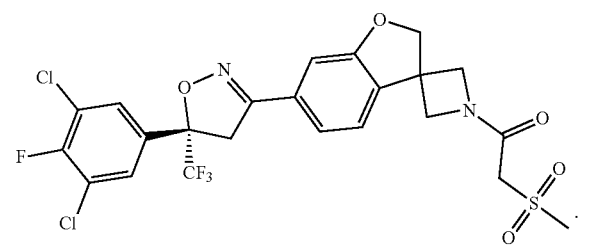

Another suitable veterinary acceptable isoxazoline is afoxolaner (NexGard®), 4-(5-(3-chloro-5-(trifluoromethyl)phenyl)-5-(trifluoromethyl)-4,5-dihydroisoxazol-3-yl)-N-(2-oxo-2-((2,2,2-trifluoroethyl)amino)ethyl)-1-naphthamide, and stereoisomers thereof, the compound of Formula (A2)

(A2)

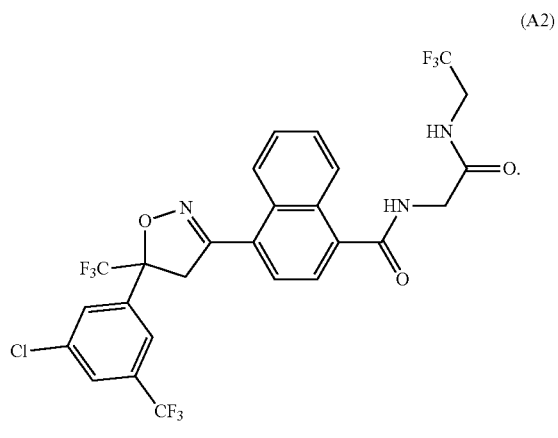 [SMILES: O=C(CNC(=O)c1ccc(C2=NOC(c3cc(Cl)cc(C(F)(F)F)c3)(C(F)(F)F)C2)c2ccccc12)NCC(F)(F)F]

Another suitable veterinary acceptable isoxazoline is fluralaner (Bravecto®), 4-(5-(3,5-dichlorophenyl)-5-(trifluoromethyl)-4,5-dihydroisoxazol-3-yl)-2-methyl-N-(2-oxo-2-((2,2,2-trifluoroethyl)amino)ethyl)-benzamide, and stereoisomers thereof, the compound of Formula (A3)

(A3)

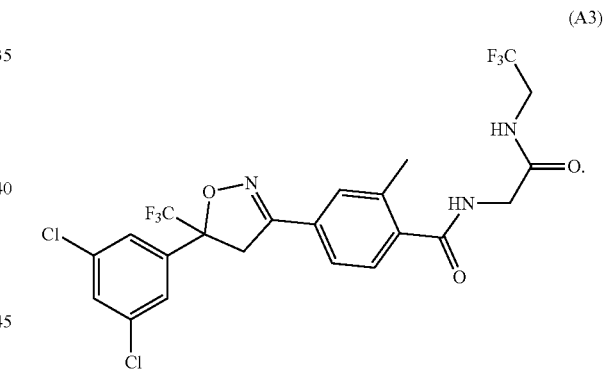

Another suitable veterinary acceptable isoxazoline is lotilaner (Credelio®), 3-methyl-N-{2-oxo-2-[(2,2,2-trifluoroethyl)amino]ethyl}-5-[(5S)-5-(3,4,5-trichlorophenyl)-5-(trifluoromethyl)-4,5-dihydro-1,2-oxazol-3-yl]thiophene-2-carboxamide, and stereoisomers thereof, the compound of Formula (A4)

(A4)

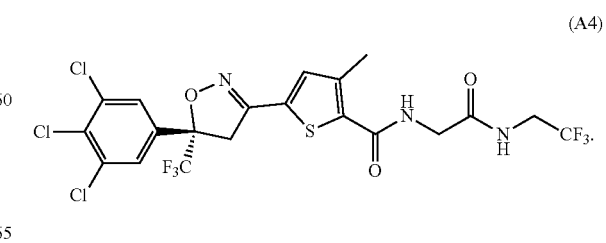

The preferred isoxazoline of the composition of the invention is sarolaner.

Macrocyclic lactones act as GABA agonists and also bind to glutamate-gated chloride channels in nerve and muscle cells of invertebrates. In both cases, these actions block the transmission of neuronal signals of the parasites, which are either paralyzed and expelled out of the body; or starved. They also affect the reproduction of some parasites by diminishing oviposition or inducing an abnormal oogenesis. The macrocyclic lactone contained within the composition is selected from the group consisting of moxidectin, ivermectin, avermectin, selamectin, dimadectin, eprinomectin, abamectin, doramectin, emamectin, milbemycin, and milbemycin oxime. The preferred macrocyclic lactone is moxidectin, milbemycin, milbemycin oxime, ivermectin, and abamectin. The more preferred macrocyclic lactone is moxidectin. The even more preferred macrocyclic lactone is stabilized moxidectin.

The composition comprising a veterinary acceptable isoxazoline and stabilized macrocyclic lactone, also comprises an acceptable salt form of pyrantel. The salt forms of pyrantel include the pamoate (embonate), citrate, and tartrate salts. The composition comprises the isoxazoline, sarolaner, stabilized moxidectin, and pyrantel pamoate. The composition also comprises at least one veterinary acceptable excipient. The composition optionally comprises at least one additional veterinary antiparasitic agent selected from the group consisting of: insect growth regulators (IGR's) (including juvenile hormone mimics and chitin synthesis inhibitors), for example: azadirachtin, diofenolan, fenoxycarb, hydroprene, kinoprene, methoprene, pyriproxyfen, tetrahydroazadirachtin, 4-chloro-2(2-chloro-2-methyl-propyl)-5-(6-iodo-3-pyridylmethoxy)pyridazine-3 (2H)-one, chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoro-ethoxy)-phenylurea and 1-(2,6-difluorobenzoyl)-3-(2-fluoro-4-trifluoromethyl)phenylurea; benzimidazole agents (e.g., thiabendazole, oxibendazole, mebendazole, fenbendazole, oxfendazole, albendazole, and triclabendazole); febantel, levamisole, morantel, praziquantel, closantel, clorsulon, and amino acetonitrile active agents, and combinations thereof. The preferred additional antiparasitic agent is selected from the group consisting of praziquantel, clorsuron, lufenuron, and triclabendazole. Preferably, the additional antiparasitic agent is praziquantel.

Macrocyclic lactones, for example, moxidectin and doramectin, are acid labile molecules and are susceptible to degradation. Combination products containing these compounds with other antiparasitics, e.g., levamisole, are generally stabilized with starches, celluloses, and amino-sugars like meglumine. Stabilizing agents include, for example, glycerol formal, amino sugars (e.g., glucosamine, tromethamine, meglumine, and the like), glycol ethers, modified starches, for example hydroxypropyl starch phosphate; cellulose derivatives (e.g., hydroxypropylmethyl cellulose (HPMC), ethyl cellulose, hydroxypropylmethyl cellulose acetyl succiante, carboxymethyl cellulose, and the like); and non-ionic triblock copolymers (e.g., Poloxamer-101, -108, -124, -188, -215, -284, -338, -407, and the like) can be used to physically stabilize the macrocyclic lactone.

In the composition of the invention, moxidectin is stabilized with a combination of stabilizing agents and optionally, at least one antioxidant. In the composition, the moxidectin is stabilized with hydroxypropylmethyl cellulose and meglumine and further stabilized with the antioxidant, BHT.

Antioxidants can also be used to help stabilize the sarolaner, pyrantel pamoate, and any of the combined excipients, in part (compositional granulations and common blend) or whole tablet. The BHT was incorporated into the moxidectin granulation. Other antioxidants can also be used to stabilize the composition, for example butylated hydroxyanisole (BHA), propyl gallate, ascorbic acid, tocopherols, tertiary butylhydroquinone, and mixtures thereof.

The amount of moxidectin (about 0.03 w/w %) in the composition is very low. Degradation can easily lead to a combination product with sub-therapeutic levels of moxidectin. Moxidectin degradants include the acid catalyzed degradants 23-Z-moxidectin and 23-keto-alpha moxidectin as well as base catalyzed degradants delta-2-moxidectin and 2-epimer moxidectin. In addition to stability, the low amount of moxidectin can also lead to content uniformity issues. To overcome moxidectin degradation and content uniformity and to ensure a stable homogenous composition, moxidectin was stabilized with a cellulose derivative. A spray granulation process was developed for granulating the moxidectin. Moxidectin is physically separated from the other active ingredients (sarolaner and pyrantel pamoate) and some veterinary acceptable excipients by converting it into an in-situ moxidectin-polymer dispersion during the granulation process thereby providing a physical barrier around the moxidectin particles. Besides stability, the HPMC also aids in the homogeneous distribution of moxidectin in the granulation as well as in the final tablet composition to ensure content uniformity. An additional stabilizer and antioxidant were added to the moxidectin granulation to provide added stability to ensure longer shelf-life of the final drug product.

The moxidectin granulation was developed separately from the sarolaner-pyrantel pamoate granulation compositions. For the moxidectin granulation, four different polymers were screened. Initially, the moxidectin-polymer ratio was about 1:160 (about 21.82 w/w % polymer of intra granular portion). The polymers included hypromellose [hydroxypropylmethyl cellulose (HPMC), Poloxamer 188 (P188), ethyl cellulose, and hydroxypropyl methyl cellulose acetyl succinate MG (HPMC AS MG). The granulates were individually blended with the sarolaner-pyrantel granulate with the addition of at least one veterinary acceptable excipient and solvent, compressed, and placed on accelerated (40° C./75% RH) stability. From these studies, moxidectin was found to significantly degrade (16.7% at 2-months) without the use of a polymer. Use of the polymers in the moxidectin granulation process provided stability to the moxidectin. HPMC (3.6%) was found to be the most effective in stabilizing moxidectin compared with P188 (5.2%), ethyl cellulose (7.4%), and HPMC AS MG (12.1%) at 3-months. A 6-month stability study of compressed tablets manufactured with HPMC showed a total moxidectin degradation of about 5-6% at accelerated stability. HPMC concentration was then assessed to determine the effect on moxidectin stability in compressed tablets. Concentrations of moxidectin:HPMC were 1:20, 1:80, 1:120, and 1:160 in the moxidectin granulation. These amounts accounted for about 2.72 w/w %, 10.91 w/w %, 16.36 w/w %, and 21.82 w/w % of the moxidectin granulation, respectively. At 6 months accelerated stability, respective moxidectin degradation values in the finished product were 5.04%, 2.41%, 2.26%, and 1.75%. Although the best stability was achieved using the 1:160 ratio of moxidectin to HPMC, it was found that the viscosity of the solution above 1:80 was not suitable for spray granulation. Therefore, the 1:80 ratio of moxidectin to HPMC was used to prepare the moxidectin granulations. The amount of HPMC in the moxidectin granulation is about 6 to 18 w/w %; the preferred amount is about 10 to 12 w/w %; and the most preferred amount is about 11 w/w %. In the final composition, the amount of HPMC is about 2.0 w/w % to about 4.0 w/w % of the total tablet weight; and more preferably, about 2.0 to 3 w/w % of the total tablet weight; and even more preferably, about 2.0 to 2.5 w/w % of the total tablet weight.

To further control moxidectin degradation, the stability enhancer, meglumine, and the antioxidant, BHT, were added to the moxidectin granulation. Moxidectin degradation at 3 months (40°/75% RH) in the final tablets with varying amounts of meglumine in the moxidectin granulation was about 2.4%, about 1.0%, and about 0.7% for the respective meglumine amounts of 0 w/w %, 1.36 w/w % (0.27 w/w % of tablet) and 2.72 w/w % (0.54 w/w % of tablet). Use of the higher concentration (2.72 w/w %) of meglumine was used initially to better control the acid catalyzed degradants. However, at 6 months, there was a greater increase in base catalyzed degradation of moxidectin at this concentration of meglumine. To minimize this additional degradation, the amount of meglumine in the moxidectin granulation was reduced slightly to about 1 to 2 w/w %; preferably about 1.2 to 1.5 w/w %; and more preferably, about 1.4 w/w %, accounting for about 0.3 w/w % of the total tablet weight. Similarly, moxidectin degradation was assessed using varying amounts of BHT in the moxidectin granulation. Moxidectin degradation in the granulation at 3 months (40°/75% RH) in the final tablets for varying amounts of BHT in the moxidectin granulation was about 2.7%, about 1.4%, about 2.3%, and about 2.2% for the respective BHT amounts of 0 w/w %, 0.095 w/w % (0.018 w/w % of tablet), 0.19 w/w % (0.037 w/w % of tablet), and 0.38 w/w % (0.074 w/w % of tablet). To further minimize moxidectin degradation, the amount of BHT in the moxidectin granulation is about 0.05 to 0.5 w/w %; preferably about 0.07 to 0.3 w/w %; more preferably about 0.08 to 0.2 w/w %; and most preferred about 0.09 to 0.1 w/w %; which accounts for about 0.02 w/w % of the total tablet weight.

In one stability study, moxidectin stability in the final compressed tablets is shown below in Table 1. Stability results represent the initial/12-month results. The 3 mg-S tablet represents 3 mg sarolaner, 0.06 mg moxidectin, and 12.5 mg pyrantel. The 6 mg-S tablet represents 6 mg sarolaner, 0.12 mg moxidectin, and 25 mg pyrantel. The 12 mg-S tablet represents 12 mg sarolaner, 0.24 mg moxidectin, and 50 mg pyrantel. The 24 mg-S tablet represents 24 mg sarolaner, 0.48 mg moxidectin, and 100 mg pyrantel. The 48 mg-S tablet represents 48 mg sarolaner, 0.96 mg moxidectin, and 200 mg pyrantel. The 72 mg-S tablet represents 72 mg sarolaner, 1.44 mg moxidectin, and 300 mg pyrantel.

TABLE 1

Moxidectin Stability (%) Results of Compressed Tablets

| Tablet | 3 mg-S | 6 mg-S | 12 mg-S | 24 mg-S | 48 mg/S | 72 mg-S |
|---|---|---|---|---|---|---|
| 25° C./ 60% RH | 4.1/3.8 | 3.8/3.4 | 3.4/3.6 | 3.9/3.3 | 4.1/4.4 | 3.9/5.0 |
| 40° C./ 75% RH | 4.1/3.6 | 3.8/3.6 | 3.4/3.6 | 3.9/3.8 | 4.1/3.7 | 3.9/3.5 |

The composition comprises at least one natural animal based palatant. Palatants are used to alter or enhance the flavor(s) of natural food products such as meats and vegetables and can be used to create additional flavor for food products that do not have the desired flavors such as snacks and oral medications. Most types of palatants are focused on scent and taste. Artificial palatants are chemically synthesized compounds that are used to flavor food items and are often formulated with the same chemical compounds found in natural palatants. Most artificial flavors are specific and often complex mixtures of singular naturally occurring flavor compounds to either imitate or enhance a natural flavor. These mixtures are formulated by flavorists to give a food product a unique flavor and to maintain flavor consistency between different product batches or after recipe changes. The list of known flavoring agents (palatants) includes thousands of molecular compounds, and can be combined to achieve flavors like chicken, turkey, beef, pork, lamb, fish, egg, cheese, seafood, smoke, and many others. A natural palatant is defined as the essential oil, oleoresin, essence or extract, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or any other edible portions of a plant, meat, seafood, poultry, eggs, dairy products, or fermentation products thereof; and can include a sweetener like sucrose and confectioner sugar; whose primary function in food is flavoring rather than nutritional. Natural palatants include animal based palatants derived from chicken, turkey, beef, pork, lamb, fish, egg, and cheese; non-animal based palatants include flavorings from fish, shrimp and other seafood, vegetable and vegetable matter. Palatants include mixtures of natural, synthetic, animal based, and non-animal based flavors/palatants. Yeast extracts are also included in the natural palatable flavors. Natural animal meat based palatants can be obtained from meat, meat products, organ meat, and mixtures thereof. For example, an oral veterinary composition medication might include animal based and/or non-animal based flavorings such as dried or powdered meat and meat parts such as beef, pork, chicken, turkey, fish, and lamb; organ meats such as liver and kidney; meat meals, bone meals and ground bone; and animal-derived food such as casein, milk (which may include dry forms and lowered fat forms, such as dry skim milk), yogurt, gelatin, cheese and egg (collectively, "animal origin flavorings") may be utilized. The natural products may or may not be sterilized by heat or other types of radiation, e.g., gamma-radiation. The preferred palatant for the composition is a natural animal based palatant. The composition contains a natural animal based palatant in an amount of about 8 w/w % to about 12 w/w % of the total weight of the tablet. The preferred amount of the natural animal based palatant is about 8 w/w % to about 11 w/w % of the total weight of the tablet. The more preferred amount of the animal based palatant is about 8 w/w % to about 10 w/w % of the total weight of the tablet. The natural animal based palatant is a component of a palatant admixture containing other veterinary acceptable excipients, including other palatants, fillers, binders, and sweeteners. The natural animal based palatant makes up about 20 to 25 w/w % of the palatant admixture. The amount of the palatant admixture in the composition ranges from about 35 to about 50 w/w % of the total weight of the tablet. The preferred amount of palatant admixture in the composition ranges from about 40 to about 45 w/w % of the total weight of the tablet. The more preferred amount of palatant admixture in the composition is about 42 w/w % of the total weight of the tablet.

The palatable, hard chewable composition comprises at least one veterinary acceptable excipient. The veterinary acceptable excipient includes excipients that are construed as binders, fillers, disintegrants, lubricants, glidants, antioxidants, and colorants.

Binders are used to add cohesiveness to the separate granulations and to the final blended composition, thereby providing the necessary bonding to form a cohesive mass and to ensure a suitable compacted tablet form. These binding agents are conventionally used in direct compression tablets and are described in Lieberman et. al., Pharmaceutical Dosage Forms, 2 Ed., Vol. 1, (1990). Non-limiting examples of veterinary acceptable binders include, but are not limited to: microcrystalline cellulose, carboxymethyl cellulose, sodium carboxy methyl cellulose, hydroxypropyl cellulose (HPC), polyvinylpyrrolidone (e.g., PVP, povidone (Kollidon 25, 30, and 90) and co-povidone (Kollidon VA 64), polyethylene glycol, acacia, corn syrup solids, tragacanth gum, gelatin, carnauba wax, alginate, and mixtures thereof. The preferred binding agents for the composition carboxymethyl cellulose, HPC, PVP, polyethylene glycol, corn syrup solids, gelatin, and mixtures thereof. HPMC can also be considered a binding agent as it does provide some binding qualities to the moxidectin granulation, however, for purposes of this composition, it is defined as a stabilizing agent (stabilizer). The amount of binding agent(s), not including HPMC, in the composition is about 6 to 10 w/w % of the total weight of the tablet. The preferred amount of binding agent(s) in the composition is about 7 to 9 w/w % of the total weight of the tablet.

The composition comprises at least one veterinary acceptable excipient that is a disintegrant, thereby providing a means for the dosage form to expand and dissolve more readily when wet and to break apart when chewed. Disintegrants are conventionally used in direct compression tablets and are also described in Lieberman et al., Pharmaceutical Dosage Forms, 2 Ed., Vol. 1, (1990). Non-exclusive examples of veterinary acceptable disintegrants include: starch including pregelatinized and modified starches, microcrystalline cellulose, methyl cellulose, carboxymethyl cellulose, carboxymethyl cellulose sodium, crospovidone, magnesium aluminum silicate, guar gum, alginic acid, sodium alginate, calcium alginate, chitosan, croscarmellose sodium (e.g., Ac-Di-Sole), sodium starch glycolate, and the like, and mixtures thereof. Preferred disintegrant(s) are selected from the group consisting of starch, carboxymethyl cellulose sodium, crospovidone, croscarmellose sodium, and sodium starch glycolate, and mixtures thereof. The more preferred disintegrant is sodium starch glycolate, crospovidone, and mixtures thereof. The amount of disintegrant in the composition is about 10 to about 18 w/w % of the total weight of the tablet. The preferred amount of disintegrant in the composition is about 12 to 16 w/w % of the total weight of the tablet. The more preferred amount is about 14 to 16 w/w % of the total weight of the tablet.

The composition comprises at least one veterinary acceptable excipient that is a filler. Non-limiting examples of fillers include: starch (e.g., corn, potato, tapioca, and the like), sugars (e.g., lactose, fructose, mannitol, and the like, including hydrous and anhydrous forms), cellulose (e.g., methyl cellulose, ethyl cellulose, and the like), calcium phosphate, soy protein fines, corn cob, corn gluten meal, wheat germ, and the like, and mixtures thereof. Preferred fillers include lactose monohydrate, soy protein fines, wheat germ, calcium phosphate, and mixtures thereof. The amount of filler is about 35 to 52 w/w % of the total weight of the tablet. The preferred amount of filler is about 40 to 48 w/w % of the total weight of the tablet. The more preferred amount of filler is about 42 to 46 w/w % of the total weight of the tablet.

The composition comprises at least one veterinary acceptable excipient that is an antioxidant. Non-exclusive examples of antioxidants include: ascorbic acid, vitamin E (tocopherol), vitamin E derivatives, sodium metabisulphate, ascrobyl palmitate, fumaric acid, citric acid, malic acid, sodium ascorbate, butylated hydroxanisole (BHA), butylated hydroxytoluene (BHT), propyl gallate, thioglycerol, and the like, and mixtures thereof. Preferred antioxidants include BHA, BHT, citric acid, and propyl gallate, and mixtures thereof. The more preferred antioxidant is BHT which was also used as a stabilizing agent for moxidectin. The amount of antioxidant in the composition is about 0.01 w/w % to about 0.05 w/w % of the total weight of the tablet. The preferred amount of antioxidant is about 0.01 w/w % to about 0.03 w/w % of the total weight of the tablet. The more preferred amount antioxidant is about 0.02 w/w % of the total weight of the tablet.

The composition comprises at least one veterinary acceptable excipient that is a glidant and a lubricant. Glidants are used to enhance product flow by reducing inter-particulate friction. Non-limiting glidants include talc and colloidal silicon dioxide. The preferred glidant is colloidal silicon dioxide. The amount of glidant in the composition is about 0.25 to 0.75 w/w % of the total weight of the tablet. The preferred amount of glidant in the composition is about 0.4 to 0.6 w/w % of the total weight of the tablet. The more preferred amount of glidant in the composition is about 0.5 w/w % of the total weight of the tablet. Lubricants are used to reduce friction during tablet ejection between the walls of the tablet and the walls of the tablet die cavity from which the tablet was formed. Non-limiting lubricants include magnesium stearate, boric acid, sodium benzoate, sodium oleate, sodium acetate, sodium lauryl sulfate, magnesium lauryl sulfate, and mixtures thereof. The preferred lubricant is magnesium stearate. The amount of lubricant in the composition is about 0.5 to 1 w/w % of the total weight of the tablet. The preferred amount of lubricant in the composition is about 0.75 w/w % of the total weight of the tablet.

The composition can comprise at least one veterinary acceptable excipient that is a colorant. Colorants can be added to the composition to enhance its physical appearance. The amount of colorant in the composition is about 0.5 w/w % to about 1.5 w/w %, and preferably, about 1 w/w % of the total weight of the tablet.

The composition is prepared using at least one solvent. The solvent is used for dissolving, suspending, and blending operations to prepare separate granulation components. The granulations are dried prior to subsequent processing, and therefore, the solvents evaporate from the granulation. However, residual solvents may exist in the final compositional blend and/or compressed tablets. The residual solvents may evaporate further over time. Solvents include water, ethanol, and mixtures thereof.

The composition is prepared by general granulation, blending, milling, sieving, and compression procedures.

The moxidectin granulation is prepared by: 1) dissolving meglumine in at least one solvent; 2) suspending HPMC in ethanol and then dissolving the suspension in water; 3) dissolving moxidectin in a solvent with BHT; 4) mixing the HPMC solution and the moxidectin solution to prepare a moxidectin granulating solution, i.e., the moxidectin-polymer dispersion; 5) dry blending at least one filler with a disintegrant; 6) spray drying the meglumine solution onto the dry blended filler and disintegrant to prepare a meglumine granulate; 7) spray dry the moxidectin granulating solution onto the meglumine granulate to prepare the stabilized moxidectin granulation; and 8) dry and mill the stabilized moxidectin granulation. The final moxidectin granulation comprises about 19 to 20 w/w % of the final weight of the tablet; accounting for about 0.027 w/w % (~0.03 w/w %) moxidectin of the final tablet weight.

The sarolaner and pyrantel pamoate granulation is prepared by: 1) dry blending sarolaner and pyrantel pamoate with a disintegrant, filler, and colorant; 2) preparing a binder solution with a solvent and binder; 3) blending the sarolaner and pyrantel pamoate blend with the binder solution and at least one additional solvent to prepare a sarolaner-pyrantel granulate in a high-shear mixer granulator; 4) dry and mill the sarolaner-pyrantel granulate. The final sarolaner/pyrantel granulation comprises about 25 to 26 w/w % of the total tablet weight; and accounting for about 1.33 w/w % sarolaner and 16 w/w % pyrantel pamoate of the final tablet weight.

The palatable admixture is also a granulation that is prepared by mixing palatants with fillers, binders, and a sweetener with water in a fluid bed granulator; drying and milling the final granulation. The final palatable granulation (palatant admixture) comprises about 35 to 50 w/w % of the final weight of the tablet; preferably about 40 to 45 w/w % of the final weight of the tablet; and more preferably about 42 w/w % of the final weight of the tablet.

The final dry blend is prepared by: 1) blending at least one disintegrant with a colorant and glidant to prepare a colored disintegrant/glidant mixture; 2) blending the palatable granulation (palatable admixture), sarolaner-pyrantel pamoate granulation, and stabilized moxidectin granulation with the colored disintegrant/glidant mixture; 3) blending the mixture with a lubricant and compressing the blend into finished palatable hard chewable tablets.

The final compositional blend is a common blend and can be used to prepare tablets of different sizes and shapes with a consistent w/w % distribution of active ingredients (moxidectin, sarolaner, and pyrantel), stabilizing agents, fillers, binders, palatants, colorants, sweeteners, and antioxidants. The compressed tablets are packaged.

The composition comprises about 1.33 w/w % of sarolaner. Tablet strengths and sizes contain different amounts of sarolaner. For example, each tablet can contain about 1 mg to about 100 mg of sarolaner. In one aspect, the tablet can contain about 1 mg, 3 mg, 5 mg, 6 mg, 8 mg, 10 mg, 12 mg, 15 mg, 20 mg, 24 mg, 30 mg, 40 mg, 48 mg, 50 mg, 60 mg, 65 mg, 68 mg, 70 mg, 72 mg, 75 mg, 80 mg, 84 mg, 88 mg, 92 mg, 96 mg, and 100 mg of sarolaner. Fractional amounts or sarolaner are also contemplated. A preferred tablet dosage amount of sarolaner is about 3 mg/tablet, 6 mg/tablet, 12 mg/tablet, 24 mg/tablet, 48 mg/tablet, and 72 mg/tablet. Dosage amounts in the different tablet strengths are used to accommodate animals of different weights such that each animal can receive a 1.2 mg/kg therapeutically effective amount of sarolaner.

The composition comprises about 0.03 w/w % (i.e., 0.027 w/w %) of moxidectin based on the total weight of the tablet. Tablet strengths and sizes contain different amounts of moxidectin. For example, tablets can contain about 0.01 mg to about 3.6 mg of moxidectin. Preferably, tablets can contain about 0.01 mg, 0.03 mg, 0.06 mg, 0.08 mg, 1.0 mg, 1.2 mg, 1.4 mg, 1.6 mg, 1.8 mg, 2.0 mg, 2.2 mg, 2.4 mg 2.6 mg, 2.8 mg, 3.0 mg, 3.2 mg, 3.4 mg, and 3.6 mg of moxidectin. Fractional amounts of moxidectin are also contemplated. A preferred tablet amount of moxidectin is about 0.06 mg/tablet, 0.12 mg/tablet, 0.24 mg/tablet, 0.48 mg/tablet, 0.96 mg/tablet, and 1.44 mg/tablet. Dosage amounts in the different tablet strengths are used to accommodate animals of different weights such that each animal can receive a 24 µg/kg therapeutically effective amount of moxidectin.

The composition comprises about 16 w/w % of pyrantel pamoate based on the total weight of the tablet. Tablet strengths can contain different amounts of pyrantel pamoate. For example, each tablet can contain about 15 mg to about 1000 mg of pyrantel pamoate. For example, the tablet can contain about 30 mg, 36 mg, 54 mg, 72 mg, 108 mg. 144 mg, 216 mg, 288 mg, 432 mg, 576 mg, 721 mg, and 865 mg of pyrantel pamoate per tablet. Fractional amounts of pyrantel pamoate are also contemplated. The preferred tablet dosage amount of pyrantel pamoate is 36.03 mg/tablet, 72.06 mg/tablet, 144.12 mg/tablet, 288.24 mg/tablet, 576.48 mg/tablet, and 864.72 mg/tablet. Respective weights of pyrantel (free base) are 12.5 mg/tablet, 25 mg/tablet, 50 mg/tablet, 100 mg/tablet, 200 mg/tablet, and 300 mg/tablet. Dosage amounts in the different tablet strengths are used to accommodate animals of different weights such that each animal can receive a 5 mg/kg therapeutically effective amount of pyrantel.

The preferred tablet strengths of each active agent (sarolaner, moxidectin, and pyrantel) for the tableted composition includes: 1) 3 mg sarolaner, 0.06 mg moxidectin, and 12.5 mg pyrantel; 2) 6 mg sarolaner, 0.12 mg moxidectin, and 25 mg pyrantel; 3) 12 mg sarolaner, 0.24 mg moxidectin, and 50 mg pyrantel; 4) 24 mg sarolaner, 0.48 mg moxidectin, and 100 mg pyrantel; 5) 48 mg sarolaner, 0.96 mg moxidectin, and 200 mg pyrantel; and 6) 72 mg sarolaner, 1.44 mg moxidectin, and 300 mg pyrantel. Tablet weights range from about 225 mg for the 3 mg sarolaner tablet to about 5400 mg for the 72 mg sarolaner tablet. The common blend composition and different size/strength tablets provide a therapeutic dose of about 1.2 mg/kg sarolaner, 24 µg/kg moxidectin, and 5 mg/kg pyrantel. The actual amounts of active agent (sarolaner, moxidectin, and pyrantel) in the final compositional blend and tablets are calculated based on potency.

The composition of the invention is useful for the treatment of parasitic worms (i.e., endoparasites), categorized as cestodes (tapeworms), nematodes (roundworms) and trematodes (flatworms or flukes); and more particularly gastrointestinal nematodes like round worms and hook worms; and other nematodes like heart worm (*Dirofilaria* and *Angiostrongylus*). The gastrointestinal roundworms include, for example, *Ostertagia ostertagi* (including inhibited larvae), *O. lyrata*, *Haemonchus placei*, *H. similis*, *H. contortus*, *Toxocara canis*, *T. leonina*, *T. cati*, *Trichostrongylus axei*, *T. colubriformis*, *T. longispicularis*, *Cooperia oncophora*, *C. pectinata*, *C. punctata*, *C. surnabada* (syn. *mcmasteri*), *C. spatula*, *Ascaris suum*, *Hyostrongylus rubidus*, *Bunostomum phlebotomum*, *Capillaria bovis*, *B. trigonocephalum*, *Strongyloides papillosus*, *S. ransomi*, *Oesophagostomum radiatum*, *O. dentatum*, *O. columbianum*, *O. quadrispinulatum*, *Trichuris* spp., and the like. Other parasites include: hookworms (e.g., *Ancylostoma caninum*, *A. tubaeforme*, *A. braziliense*, *Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis*, *H. lineatum*, *Dermatobia hominis*); kidneyworms (e.g., *Stephanurus dentatus*); screw worm (e.g., *Cochliomyia hominivorax* (larvae); filarial nematodes of the superfamily Filarioidea and the Onchocercidae Family. Non-limiting examples of filarial nematodes within the Onchocercidae Family include the genus *Brugia* spp. (i.e., *B. malayi*, *B. pahangi*, *B. timori*, and the like), *Wuchereria* spp. (i.e., *W. bancrofti*, and the like), *Dirofilaria* spp. (*D. immitis*, *D. repens*, *D. ursi*, *D. tenuis*, *D. spectans*, *D. lutrae*, and the like), *Dipetalonema* spp. (i.e., *D. reconditum*, *D. repens*, and the like), *Onchocerca* spp. (i.e., *O. gibsoni*, *O.* gutturosa, O. volvulus, and the like), *Elaeophora* spp. (*E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*). In another aspect of the invention, the composition of the present invention is useful for treating endoparasiticidal infection from filarial nematodes within the genus *Dirofilaria* (i.e., *D. immitis, D. repens, D. ursi, D. tenuis*, and the like). In another aspect of the invention, the composition is useful for treating angiostrongylosis caused by *Angiostrongylus vasorum* (i.e., French heartworm; lungworm).

The composition of the invention is also useful for the treatment of ectoparasites. Some non-limiting examples of ectoparasites include: ticks (e.g., *Ixodes* spp., (e.g., *I. ricinus, I. hexagonus*), *Rhipicephalus* spp., (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Sarcoptes* spp., (e.g., *S. scabiei*), *Psoroptes* spp., (e.g., *P. bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies and sand flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*).

The composition of the present invention is of particular value for the control of ectoparasites and endoparasites which are injurious to and/or spread or act as vectors of diseases in companion animals and livestock, and to humans, particularly in companion animals, preferably canine. For example, ticks can transmit microorganisms that cause Lyme disease, ehrlichiosis, Rocky Mountain spotted fever, anaplasmosis, hepatozoonosis, and babesiosis.

EXAMPLES

The invention is further described by the following compositional example which further illustrates the invention, and is not intended, nor should it be interpreted, to limit the scope of the invention.

Palatable, hard chewable compositions containing sarolaner, moxidectin, and pyrantel pamoate were prepared and evaluated for palatability, stability, safety, and efficacy. Example 1 describes the stable, palatable composition.

Example 1. Common Blend-Composition

| Excipient(s)/Active | ~w/w % of Total Tablet |
|---|---|
| sarolaner | 1.3 |
| moxidectin | 0.03 |
| pyrantel pamoate | 16.0 |
| stabilizer | 2.4 |
| disintegrant | 15.2 |

Example 1. Common Blend-Composition

| Excipient(s)/Active | ~w/w % of Total Tablet |
|---|---|
| glidant and lubricant | 1.25 |
| palatant admixture* | 42 |
| colorant | 1 |
| filler | 19.7 |
| binder | 1.1 |
| antioxidant | 0.02 |
| Total | 100 |

*Admixture includes at least one natural animal based palatant; and at least one each of a natural palatant, sweetener, filler, and binder. The tabulated binder and filler amounts are exclusive to those within the palatable admixture.

Biological

The composition (common blend) was compressed into at least six (6) different tablet strengths and sizes to accommodate a range of dog weights; such that each dog will receive, on average, about 1.2 mg/kg sarolaner; 5 mg/kg pyrantel; and 24 μg/kg moxidectin; i.e., the combination product. The palatable, hard chewable tablets are administered orally, once a month, to treat and prevent endoparasitic and ectoparasitic infections and infestations in animals, preferably canines.

Palatability

In a palatability study, 32 beagle dogs were randomized in a cross-over study design. Dogs were provided placebo hard chewable tablets or the combination product (test). Placebo and test products comprised the same palatant admixture. Placebo and test tablet consumption was voluntary. There was a 2-day washout period between treatments. Palatability (n=64) was calculated at 87.5% for the placebo and 84.4% for the combination product. Overall, the composition was shown to be palatable in dogs.

Safety/Efficacy

Collectively, oral administration of moxidectin at 24 μg/kg provides robust and improved prevention of heartworm disease caused by susceptible and macrocyclic lactone (ML) ML-resistant *D. immitis* strains currently circulating in dogs, while maintaining an adequate margin of safety in all dogs, including ML-sensitive Collies. Three monthly doses of a 24 μg/kg provided a 98.8% (JYD-34), 99.5% (ZoeLA) and 99.5% (ZoeMO) rate of efficacy against ML-resistant strains of *D. immitis* isolates. Efficacy was 100% against sensitive isolates after a single dose. Results were no different when moxidectin was combined with sarolaner and pyrantel, showing non-interference of actives. Overall, a single oral dose of the combination product (moxidectin, sarolaner, and pyrantel) was 100% effective in preventing development of *D. immitis* in dogs inoculated with infective $L_3$ 30 days before treatment. In another study, the combination product prevented angiostrongylosis by reducing the level of infection with immature adult (L5) stages of *Angiostrongylus vasorum*.

Tick studies were conducted in fed and fasting dogs. The fed combination product treated group had a 100% reduction in live tick counts 48 hours after treatment of the existing infestation, and ≥97.2% reduction in live tick counts 48 hours after weekly re-infestations for 35 days. Live tick counts for the combination product group were significantly lower than the placebo group (P≤0.0039) on all post-treatment count days. The fasted combination product-treated group had a 99.4% reduction in live tick counts 48 hours after treatment of the existing infestation, and 100% reduction in live tick counts 48 hours after weekly re-infestations for 28 days. Live tick counts for the combination product group were significantly lower than the placebo group (P≤0.0075) on all post-treatment count days. The fed combination product-treated group had a 100% reduction in live tick counts 72 hours after treatment of the existing infestation, and 100% reduction in live tick counts 72 hours after weekly re-infestations for 36 days. Live tick counts for the combination product group were significantly lower than the placebo group (P<0.0001) on all post-treatment count days. The fasted combination product-treated group had a 100% reduction in live tick counts 72 hours after treatment of the existing infestation, and 99.4% reduction in live tick counts 72 hours after weekly re-infestations for 36 days. Live tick counts for the combination product group were significantly lower than the placebo group (P<0.0001) on all post-treatment count days. Overall, studies showed that the combination product was able to treat and control tick infestations on dogs for four to five weeks against *Amblyomma americanum, Amblyomma maculatum, Dermacentor variabilis, Dermacentor reticulatus, Ixodes* spp. (*scapularis, hexagonus, and ricinus*), and *Rhipicephalus sanguineus*.

In a flea study, the combination product treated group had a 100% reduction in live flea counts approximately 72 hours after treatment of the existing infestation, and 100% reduction in live flea counts approximately 72 hours after weekly re-infestations for 35 days. Live flea counts for the combination product group were significantly lower than the placebo group (P<0.0001) on all post-treatment count days. Overall, studies showed that the combination product had immediate and persistent flea killing activity against new infestations for five weeks against *Ctenocephalides felis* and *Ctenocephalides canis*.

The combination product was also shown to be effective in the treatment and control of roundworms (immature adult (≥95.2%) and adult (99.2%) *Toxocara canis* and adult *Toxascaris leonina*), adult hookworms (*Ancylostoma caninum* and *Uncinaria stenocephala*) in dogs and puppies 8 weeks of age and older. Because *T. canis* is the dose limiting gastrointestinal parasite for pyrantel pamoate, effectiveness of the combination product against *T. leonina, A. caninum*, and *U. stenocephala* is inferred. In addition, when compared to pre-treatment, the combination product provided a 99.2% reduction in *T. canis*, and a 99.97% reduction in *A. caninum* fecal egg counts 10 days after treatment administration.

Overall, the combination product providing a dose of 1.2 mg/kg sarolaner, 24 µg/kg moxidectin, and 5 mg/kg pyrantel was shown to be both safe and efficacious in dogs against endoparasites (i.e., gastrointestinal worms, heart (and lung) worms) and ectoparasites (fleas and ticks).

Stability

Twenty-four batches of the composition (10% scale) comprising sarolaner, moxidectin, and pyrantel pamoate were tableted into the six dosage strengths (e.g., 3 mg, 6 mg, 12 mg, 24 mg, 48 mg, and 72 mg sarolaner; with respective moxidectin and pyrantel pamoate amounts) and packaged in aluminum/aluminum blisters and placed on long-term storage in accordance with VICH guideline GL4 for 18 months at 25° C./60% RH and 30° C./65% RH and for 12 months at accelerated condition of 40° C./75% RH. RH is relative humidity. Stability was evaluated for appearance, water content, assay, antioxidant (BHT) content, degradation products, dissolution, hardness, friability, and microbiological quality. In addition, photostability of the lowest strength tablet and highest strength tablet was also evaluated in accordance with VICH GL5. Overall, the data from the stability program demonstrated that there were no significant changes in any of the measured parameters. Therefore, the compressed composition was shown to be stable.

We claim:

1. A palatable, hard chewable tablet veterinary composition comprising:
    a. a therapeutically effective amount of sarolaner;
    b. stabilized moxidectin wherein the moxidectin is stabilized with hydroxypropylmethyl cellulose and meglumine;
    c. pyrantel pamoate;
    d. at least one natural animal meat based palatant;
    e. at least one veterinary acceptable excipient; and
    f. optionally, at least one additional veterinary antiparasitic agent.

2. The composition of claim 1, wherein the hydroxypropylmethyl cellulose and meglumine are in the amount of about 2 to about 3 w/w % of the total weight of the tablet.

3. The composition of claim 1, wherein the moxidectin is further stabilized with an antioxidant.

4. The composition of claim 3, wherein the sarolaner is in the amount of about 1.3 w/w %; the stabilized moxidectin is in the amount of about 0.03 w/w %, the pyrantel pamoate is in the amount of about 16 w/w %, and the natural animal meat based palatant is admixed with at least one other natural based palatant; and wherein the w/w % amounts are based on the total weight of the tablet.

5. A method of treating or preventing a parasitic infection or infestation in an animal in need thereof, by administering a palatable, hard chewable tablet veterinary composition comprising:
    a. a therapeutically effective amount of sarolaner;
    b. stabilized moxidectin wherein the moxidectin is stabilized with hydroxypropylmethyl cellulose and meglumine;
    c. pyrantel pamoate;
    d. at least one natural animal meat based palatant;
    e. at least one veterinary acceptable excipient; and
    f. optionally, at least one additional veterinary antiparasitic agent.

6. The method of claim 5 wherein the hydroxypropylmethyl cellulose and meglumine are in the amount of about 2 w/w % to about 3 w/w % of the total weight of the tablet.

7. The method of claim 6 wherein the animal is a companion animal.

8. The method of claim 7 wherein the companion animal is canine.

9. A palatable, hard chewable tablet veterinary composition comprising:
    a. a therapeutically effective amount of sarolaner;
    b. stabilized moxidectin and wherein the moxidectin is stabilized with hydroxypropylmethyl cellulose and meglumine;
    c. pyrantel pamoate;
    d. at least one natural animal meat based palatant;
    e. at least one veterinary acceptable excipient; and
    f. optionally, at least one additional veterinary antiparasitic agent, for the treatment or prevention of a parasitic infection or infestation in an animal.

10. The composition of claim 9 wherein the hydroxypropylmethyl cellulose and meglumine are in the amount of about 2 to about 3 w/w % of the total weight of the tablet.

11. The composition of claim 10, wherein the sarolaner is in the amount of about 1.3 w/w %; the stabilized moxidectin is in the amount of about the pyrantel pamoate is in the amount of about 16 w/w %, and the natural animal meat based palatant is admixed with at least one other natural based palatant; and wherein the w/w % amounts are based on the total weight of the tablet.

12. The composition of claim 11, wherein the palatant admixture comprises about 40 to 45% of the total weight of the tablet.

\* \* \* \* \*